United States Patent
Mosesov et al.

(10) Patent No.: US 7,280,872 B1
(45) Date of Patent: Oct. 9, 2007

(54) WIRELESS COMMUNICATION WITH IMPLANTABLE MEDICAL DEVICE

(75) Inventors: Oleg Mosesov, Maple Grove, MN (US); Perry Mills, Arden Hills, MN (US)

(73) Assignee: Transoma Medical, Inc., Arden Hills, MN (US)

( * ) Notice: Subject to any disclaimer, the term of this patent is extended or adjusted under 35 U.S.C. 154(b) by 415 days.

(21) Appl. No.: 10/688,253

(22) Filed: Oct. 16, 2003

(51) Int. Cl.
*G08C 17/00* (2006.01)
*A61N 1/00* (2006.01)

(52) U.S. Cl. .............. 607/60; 607/31; 607/32; 128/903

(58) Field of Classification Search .......... 607/31, 607/32, 60; 128/903
See application file for complete search history.

(56) References Cited

U.S. PATENT DOCUMENTS

| | | | |
|---|---|---|---|
| 5,487,760 A | 1/1996 | Villafana | |
| 5,861,019 A | 1/1999 | Sun et al. | |
| 6,115,636 A | 9/2000 | Ryan | |
| 6,150,951 A | 11/2000 | Olejniczak | |
| 6,167,312 A | 12/2000 | Goedeke | |
| 6,169,925 B1 | 1/2001 | Villaseca et al. | |
| 6,240,317 B1 | 5/2001 | Villaseca et al. | |
| 6,379,300 B1 | 4/2002 | Haubrich | |
| 6,535,766 B1 | 3/2003 | Thompson et al. | |
| 2002/0042637 A1 | 4/2002 | Stover | |
| 2002/0045920 A1 | 4/2002 | Thompson | |
| 2002/0065539 A1 | 5/2002 | Von Arx et al. | |
| 2002/0095195 A1 | 7/2002 | Mass et al. | |
| 2002/0103514 A1* | 8/2002 | Abrahamson | 607/60 |
| 2002/0123776 A1 | 9/2002 | Van Arx et al. | |
| 2003/0114897 A1* | 6/2003 | Von Arx et al. | 607/60 |

OTHER PUBLICATIONS

Memorandum Opinion and Order, In the matter of Biotronik, Inc. Equipment Authorization for the Medical Implant Communications Service, FCC Identifier PG6BA0T, Adopted Feb. 12, 2003, Released Feb. 25, 2003, Before the Federal Communications Commission, Washington D.C. 20554.

* cited by examiner

*Primary Examiner*—Carl Layno
*Assistant Examiner*—Yun Haeng Lee
(74) *Attorney, Agent, or Firm*—Fish & Richardson P.C.

(57) ABSTRACT

Embodiments of the present invention are directed to apparatus and methods of minimizing current drain of an implantable medical device during wireless communication with the device, thereby reducing battery depletion of the device. In one embodiment, the implantable medical device comprises a wireless receiver configured to communicate wirelessly with an external transmitter of an external device via a plurality of communication channels each having a different frequency within a frequency band. The wireless receiver comprises a wideband receiver circuit configured to detect a signal from any of the plurality of communication channels at the different frequencies within the frequency band simultaneously. In another embodiment, the external device is configured to communicate wirelessly with the implantable medical device via a preset communication channel, and via an alternate communication channel selected according to an order of priority if the wireless receiver does not detect a suitable signal from the external transmitter using the preset communication channel.

18 Claims, 4 Drawing Sheets

WIRELESS COMMUNICATION WITH IMPLANTABLE MEDICAL DEVICE

CROSS-REFERENCES TO RELATED APPLICATIONS

Not applicable

BACKGROUND OF THE INVENTION

The present invention relates to wireless communication with implantable medical devices and, more particularly, to simple and effective ways of minimizing current drain of an implantable medical device, thereby reducing battery depletion of the implantable medical device.

Implantable medical devices can be used for monitoring various physiological conditions of a body organ. The monitoring of fluid pressure within a body organ provides an important tool for medical research and clinical diagnosis.

Blood pressure measurements are particularly important for medical research and diagnosis for a variety of reasons. Such measurements provide researchers with insight into the physiology and functioning of the heart. Blood pressure measurements also provide researchers with useful information regarding the safety and efficacy of pharmaceuticals and the toxicity of chemicals. By transducing blood pressure into a signal waveform, a variety of useful parameters can be extracted. These parameters provide valuable information for the diagnosis of heart disease.

For example, blood pressure provides useful information for controlling a cardiac rhythm management system. Cardiac rhythm management systems include, among other things, pacemakers, or pacers. Pacers deliver timed sequences of low energy electrical stimuli, called pace pulses, to the heart. Heart contractions are initiated in response to such pace pulses. By properly timing the delivery of pace pulses, the heart can be induced to contract in proper rhythm, greatly improving its efficiency as a pump. Pacers are often used to treat patients with Brady arrhythmias, that is, hearts that beat too slowly, or irregularly. Cardiac rhythm management systems also include cardioverters or defibrillators that are capable of delivering higher energy electrical stimuli to the heart. Defibrillators are often used to treat patients with tachyarrhythmia, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

Medical implants may be designed to communicate with programmer or control devices via the FCC Medical Implant Communication Service (MICS) regulations under Title 47 of the Code of Federal Regulations (CFR). 47 CFR 95.628 allows the use of the 402–405 MHz frequency band and requires transmissions of bandwidth ≦300 KHz.

BRIEF SUMMARY OF THE INVENTION

To avoid interference and improve the reliability of communication, a system may include the ability to communicate on any one of a number of channels; up to ten channels if the 3 MHz band were divided into channels of 300 KHz each. This would allow the programmer to monitor the channels and choose a channel for communication that has minimal or acceptable interference. 47 CFR 95.628-a-4 states: "If no signal in a MICS channel above the monitoring threshold power level is detected, the medical implant programmer or control transmitter may initiate a MICS communication session involving transmissions to and from a medical implant device on that channel." The initial request from the programmer to the implant may initiate a communication sessions ("request") on a "quiet" channel which the programmer has chosen. The implant may not necessarily have prior knowledge of the channel used. The implant may have some knowledge of when to expect the request.

The implant may sequentially scan (or otherwise monitor) any of the MICS channels that the programmer is capable of transmitting on to listen for a request. It may be less practical for the implant to scan continuously because the battery depletion required to do so may result in a shorter battery life.

Embodiments are directed to apparatus and methods of minimizing the current drain of an implantable medical device dedicated to wireless communication, thereby reducing battery depletion of the device. In some embodiments, the average current drain of the implantable medical device is reduced by performing the minimum required scanning for signals. In some embodiments where the implantable device is listening for a signal from a programmer, the implantable device may scan the set of channels once every five seconds which is, by regulation, the maximum time the programmer may transmit without sending data. In some embodiments, the implantable medical device may perform a scan or series of scans at a predetermined time arranged in a previous communication with the programmer. This reduces the amount of on-time for the receiver portion of the implantable medical device. In addition, the battery depletion for each scan of the channels may be reduced. For example, instead of a scan of a number of channels, a wideband receiver provided in the implantable medical device can listen for a request on any of the channels at once. In channel scanning, the programmer may be designed to transmit the request on the channel used in the last communication session unless that channel was receiving more interference than permissible. In that case, alternative channels such as the second-to-last channel used may be selected.

In accordance with an embodiment, an implantable medical device comprises a wireless receiver configured to communicate wirelessly with an external transmitter of an external device via a plurality of communication channels each having a different frequency within a frequency band. In some embodiments, the wireless receiver comprises a wideband receiver circuit configured to detect a signal from any of the plurality of communication channels at the different frequencies within the frequency band simultaneously.

In some embodiments, the frequency band is between 402 and 405 MHz, and wherein the plurality of communication channels comprise, by way of example, not limitation, n contiguous channels of (3÷n) MHz each, such as ten contiguous channels of 300 KHz each in the frequency band. The wideband receiver circuit may include a front-end filter configured to filter a signal received from the external transmitter, a low noise amplifier coupled to the front-end filter to amplify the filtered signal, a local oscillator producing an output, and a mixer coupled to the low noise amplifier and the local oscillator to multiply the output of the local oscillator with the amplified received signal from the low noise amplifier and generate a mixer output signal, the mixer being coupled to the bandpass filter which filters the mixer output signal. The wideband receiver circuit may further include a bandpass filter, an intermediate frequency amplifier coupled to the bandpass filter to be driven by an output of the bandpass filter, a demodulator coupled to the intermediate frequency amplifier to demodulate an intermediate frequency signal from the intermediate frequency amplifier to a baseband signal, and a decoder to decode the baseband signal. The bandpass filter may be a third-order filter having a center frequency of about 10.7 MHz, a passband width of about 4 MHz, and a passband ripple of about 0.1 dB.

In some embodiments, as an independent technique to reduce battery depletion the wireless receiver is configured to detect wirelessly a signal from the external transmitter at a primary predetermined time arranged in a previous communication with the external transmitter. The wireless receiver may be configured to detect wirelessly a signal from the external transmitter at a secondary predetermined time arranged in the previous communication with the external device if the wireless receiver fails to detect wirelessly a suitable signal from the external transmitter at the primary predetermined time. The wireless receiver may be configured to scan for signals from the external transmitter at preset time periods if the receiver fails to detect wirelessly a suitable signal from the external transmitter at the primary predetermined time.

According to another technique to reduce battery depletion, the implantable medical device comprises a wireless transmitter configured to communicate wirelessly with an external receiver of the external device via the plurality of communication channels, wherein the wireless transmitter is configured to transmit a signal to the external receiver via a communication channel which is used by the external transmitter to communicate with the wireless receiver of the implantable medical device as detected by the receiver circuit of the wireless receiver.

Another embodiment is directed to a method for communicating between an external device having an external transmitter and an implantable medical device having a wireless receiver. The method comprises providing a wideband receiver circuit in the wireless receiver of the implantable medical device configured to communicate wirelessly with the external transmitter via a plurality of communication channels each having a different frequency within a frequency band; and detecting with the wideband receiver circuit a signal from any of the plurality of communication channels at the different frequencies within the frequency band simultaneously.

In accordance with another embodiment, a medical communication system comprises an implantable medical device including a wireless receiver and a wireless transmitter. An external device includes an external transmitter and an external receiver configured to communicate wirelessly with the implantable medical device via a plurality of communication channels each having a different frequency within a frequency band. The external device is configured to communicate wirelessly with the implantable medical device via a preset communication channel. The external device is configured to communicate wirelessly with the implantable medical device via an alternate communication channel selected according to an order of priority if the wireless receiver does not detect a suitable signal from the external transmitter using the preset communication channel as indicated by a lack of response to the external device.

In some embodiments, the external device is configured to communicate wirelessly with the implantable medical device in a present communication session on a last communication channel used in a last communication session immediately preceding the present communication session. The external device is configured to communicate wirelessly with the implantable medical device in the present communication session on a second-to-last communication channel used in a second-to-last communication session immediately preceding the last communication session, if the wireless receiver does not detect a suitable signal from the external transmitter using the last communication channel. The order of priority of communication channels selected is based on communication channels used in previous communication sessions in reverse chronological order.

Another embodiment is directed to a method for communication between an implantable medical device having a wireless receiver and a wireless transmitter and an external device having an external transmitter and an external receiver, wherein the implantable medical device and the external device is configured to communicate wirelessly with one another via a plurality of communication channels each having a different frequency within a frequency band. The method comprises initiating a present communication session between the implantable medical device and the external device using a preset communication channel selected from the plurality of communication channels; and switching to an alternate communication channel for the present communication session according to an order of priority if the wireless receiver of the implantable medical device does not detect a suitable signal from the external transmitter of the external device using the preset communication channel. The external device would switch to an alternate communication channel based on a lack of response from the implantable medical device.

DETAILED DESCRIPTION OF THE INVENTION

A. Implantable Medical Devices

The following detailed description should be read with reference to the drawings in which similar elements in different drawings are numbered the same. The drawings, which are not necessarily to scale, depict illustrative embodiments and are not intended to limit the scope of the invention.

Figure 1:
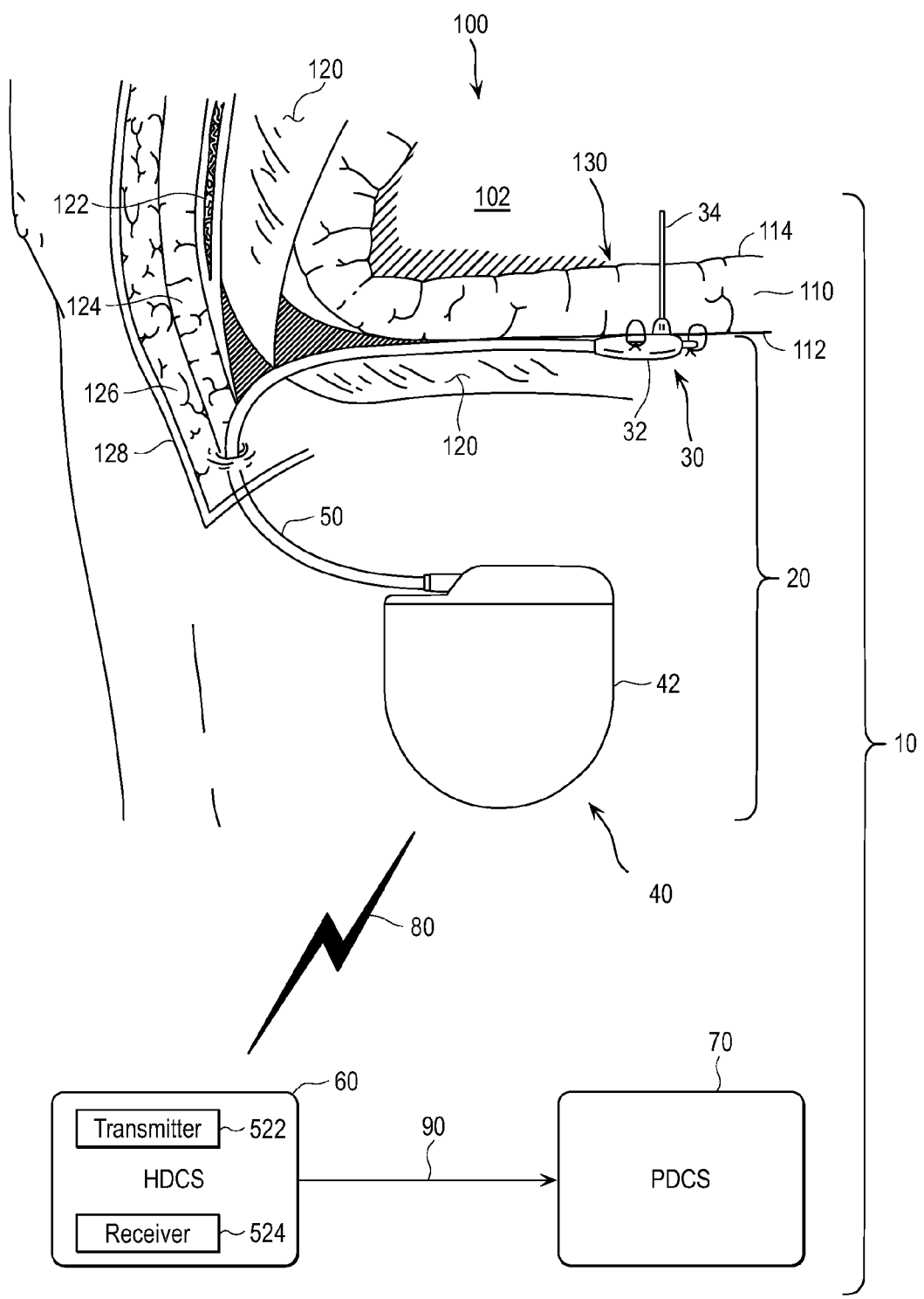
FIG. 1 is a schematic plan view of pressure monitoring system utilizing an implantable telemetry device, which includes a remote sensor assembly having a pressure transmission catheter disposed endocardially.

With reference to FIG. 1, an exemplary embodiment of a system 10 for measuring and monitoring endocardial pressure is shown. The system 10 includes an implantable telemetry device (ITD) 20, which may be partitioned into a remote sensor assembly (RSA) 30 and a telemetry unit (TU) 40 interconnected via lead 50. An alternative construction (not shown) of the ITD 20 mounts the RSA 30 and TU 40 components in a single unit which may be implanted in a manner similar to RSA 30. The RSA 30 measures endocardial pressure and the TU 40 transmits measured pressure data to a receiver located outside the body via wireless telemetry link 80.

The system 10 also includes a home (i.e., local) data collection system (HDCS) 60 which receives the telemetry signal from the TU 40 via wireless link 80. The HDCS 60 may correct for fluctuations in ambient barometric pressure, may evaluate the validity of the received signal, and, if the received signal is deemed to be valid, may extract parameters from that signal and store the data according to a physician-defined protocol.

The system 10 further includes a physician (i.e., remote) data collection system (PDCS) 70 which receives the data signal from the HDCS 60 via a telecommunication link 90 (e.g., the Internet). The PDCS 70 may display the data, and store the data according to a physician-defined protocol. With this information, the system 10 enables the treating physician to monitor endocardial pressure in order to select and/or modify therapies for the patient to better treat diseases such as CHF and its underlying causes.

For example, the system 10 may be used for assessment of pressure changes (e.g., systolic, diastolic, min dP/dt, and max dP/dt) in the main cardiac pumping chamber, the left ventricle (LV). These pressures are known to fluctuate with clinical status in CHF patients, and they provide key indicators for adjusting treatment regimens. For example, increases in end-diastolic pressure, changes in the characteristics of pressure within the diastolic portion of the pressure waveform, and either decreases in max dP/dt or increases in minimum dP/dt together suggest a deteriorating cardiac status. With this information, the physician is able to promptly and remotely adjust treatment. In addition, the system 10 may assist the physician in management of patients when newer forms of device therapy (e.g., multiple-site pacing, ventricular assist as a bridge to recovery, or implantable drugs pumps) are being considered.

The RSA 30 includes a pressure transducer and an electronics module (not visible) contained within a housing 32. The pressure transducer and the electronics module may be the same or similar to those described in U.S. Pat. Nos. 4,846,191, 6,033,366, 6,296,615 or PCT Publication WO 00/16686, all to Brockway et al., the entire disclosures of which are incorporated herein by reference. The RSA housing 32 protects the pressure transducer and the electronics module from the harsh environment of the human body. The RSA housing 32 may be fabricated of a suitable biocompatible material such as titanium and may be hermetically sealed.

The pressure transducer may be of the piezoresistive type, for example. The electronics module may provide excitation to the pressure transducer, amplify the pressure and EGM (Electrogram) signals, and digitally code the pressure and EGM information for communication to the TU 40 via the flexible lead 50. The electronics module may also provide for temperature compensation of the pressure transducer and provide a calibrated pressure signal. A temperature measurement device may be included within the electronics module to compensate the pressure signal from temperature variations.

The proximal end of the RSA housing 32 includes an electrical feedthrough to facilitate connection of the electronics module to the flexible lead 50. The distal bottom side of the housing includes a pressure transducer header to facilitate mounting of the pressure transducer and to facilitate connection to a pressure transmission catheter (PTC) 34.

The flexible lead 50 connects the electronics module of the RSA 30 to the telemetry electronics disposed in the TU 40. The lead 50 may contain, for example, four conductors—one each for power, ground, control in, and data out. The lead 50 may incorporate conventional lead design aspects as used in the field of pacing and implantable defibrillator leads. The lead 50 may optionally include one or more EGM electrodes, and the number of conductors may be modified to accommodate the EGM electrodes.

The TU 40 includes telemetry electronics (not visible) contained within housing 42. The telemetry electronics disposed in the TU 40 may be the same or similar to those described in U.S. Pat. Nos. 4,846,191, 6,033,366, 6,296,615 or PCT Publication WO 00/16686, all to Brockway et al. The TU housing 42 protects the telemetry electronics from the harsh environment of the human body. The TU housing 42 may be fabricated of a suitable biocompatible material such as titanium, ceramic, or a combination thereof, and is hermetically sealed. Examples of other suitable housing designs are disclosed in U.S. Provisional Patent Application No. 60/438,712, filed Jan. 7, 2003, entitled Housing For Implantable Telemetry Device, the entire disclosure of which is incorporated herein by reference. The outer surface of conductive (i.e., metallic) portions of the TU housing 42 may serve as an EGM sensing electrode. If a non-conductive material such as ceramic is used for the housing 42, conductive metal pads may be attached to the surface thereof to serve as EGM sensing electrodes. The TU housing 42 includes an electrical feedthrough to facilitate connection of the telemetry electronics to the lead 50.

The PTC 34 refers pressure from the pressure measurement site to the pressure transducer located inside the RSA housing 32. The PTC 34 may comprise a tubular structure with a liquid-filled lumen extending therethrough to a distal opening or port. The PTC 34 may comprise a wide variety of materials, constructions and dimensions depending on the particular clinical application and the bodily tissue in which the PTC 34 resides when implanted. Various materials and construction alternatives for the PTC 34 are described in U.S. Provisional Patent Application No. 60/454,823, filed Mar. 12, 2003, and entitled Pressure Transmission Catheter for Implantable Pressure Sensors, the entire disclosure of which is incorporated herein by reference. By way of example, not limitation, the PTC 34 may have a length of approximately 25 mm, an inside diameter of approximately 0.025 inches, and a distal shaft diameter of approximately 0.055 inches for LV pressure monitoring applications as shown and described with reference to FIG. 1. Various tapers, flares, wall thicknesses, etc. may also be incorporated into the PTC 34 without significant departure from these approximate dimensions. The PTC 34 may optionally include one or more EGM electrodes or other physiological sensors as described in U.S. Pat. No. 6,296,615 to Brockway et al.

The proximal end of the PTC 34 is connected to the pressure transducer via a nipple tube (not visible in FIG. 1), thus establishing a fluid path from the pressure transducer to the distal end of the PTC 34. A barrier such as a gel plug and/or membrane may be disposed in or over the distal opening to isolate the liquid-filled lumen of the PTC 34 from bodily fluids and to retain the fluid in the lumen, without impeding pressure transmission therethrough. In one embodiment, the fluid is chosen to be a fluorinated silicone oil and the gel is chosen to be dimethyl silicone gel. Further aspects of suitable fluids and gels are described in U.S. patent application Ser. No. 10/272,489, filed Oct. 15, 2002, entitled Improved Barriers and Methods for Pressure Measurement Catheters, the entire disclosure of which is incorporated herein by reference.

Further details and other aspects of the system 10 are described in U.S. patent application Ser. No. 10/077,566, filed Feb. 15, 2002, entitled Devices, Systems and Methods for Endocardial Pressure Measurement. Reference may also be made to U.S. Pat. No. 4,846,191 to Brockway et al., U.S. Pat. No. 6,033,366 to Brockway et al., U.S. Pat. No. 6,296,615 to Brockway et al., and PCT Publication WO 00/16686 to Brockway et al. for examples of alternative embodiments.

As seen in FIG. 1, the ITD 20 may be surgically implanted in/on a heart 100 of a patient. In this exemplary embodiment, the PTC 34 is inserted directly into the left ventricle (LV) 102 across the left ventricular wall 130 for the purpose of measuring LV pressure. In particular, the RSA housing 32 resides on the epicardium 112 in the pericardial space defined by pericardium 120, with the PTC extending across the epicardium 112, myocardium 110 and endocardium 114, and into the LV chamber 102. This allows for chronic monitoring of pressure in the LV chamber 102 of the heart 100.

Implantation of the ITD 20, including RSA 30 and TU 40, may take place during an open chest procedure such as would normally be done to perform coronary artery bypass or valve repair/replacement. Alternatively, the ITD 20 may be implanted in a separate surgical procedure. In such a case, the surgeon performs a median sternotomy, cutting across the dermal layer 128, sub-dermal tissue layer 126, muscle layer 124, and sternum 122. The surgeon then cuts the pericardial sac 120 to expose the heart 100, down to the LV apex.

The PTC 34 is introduced into the LV 102 at the inferior apical segment using a peelable sheath introducer and a trocar (not shown). The peelable-sheath introducer facilitates insertion of the PTC 34 into the myocardium 110 and protects the PTC 34 from damage that may otherwise occur during the insertion process. Following insertion of the PTC 34, the peelable sheath introducer is removed. The PTC 34 is automatically positioned within the LV 102, in terms of depth, by virtue of its length when the housing 32 of the RSA 30 contacts the epicardial surface.

The proximal lead 50 is then draped over the open pericardial edge, and brought caudally inferior laterally under the abdominal fascia. A 4–5 cm horizontal incision is made on the left upper quadrant of the abdominal wall and a subcutaneous pocket is created. The proximal end of the flexible lead 50 may be brought into the subcutaneous pocket through an introducer placed through the abdominal fascia. If a releasable connection is utilized, the lead 50 is attached to the TU 40, tested using a PDCS, and the TU 40 is placed in the subcutaneous pocket. The pocket and the chest are then closed.

Figure 2:
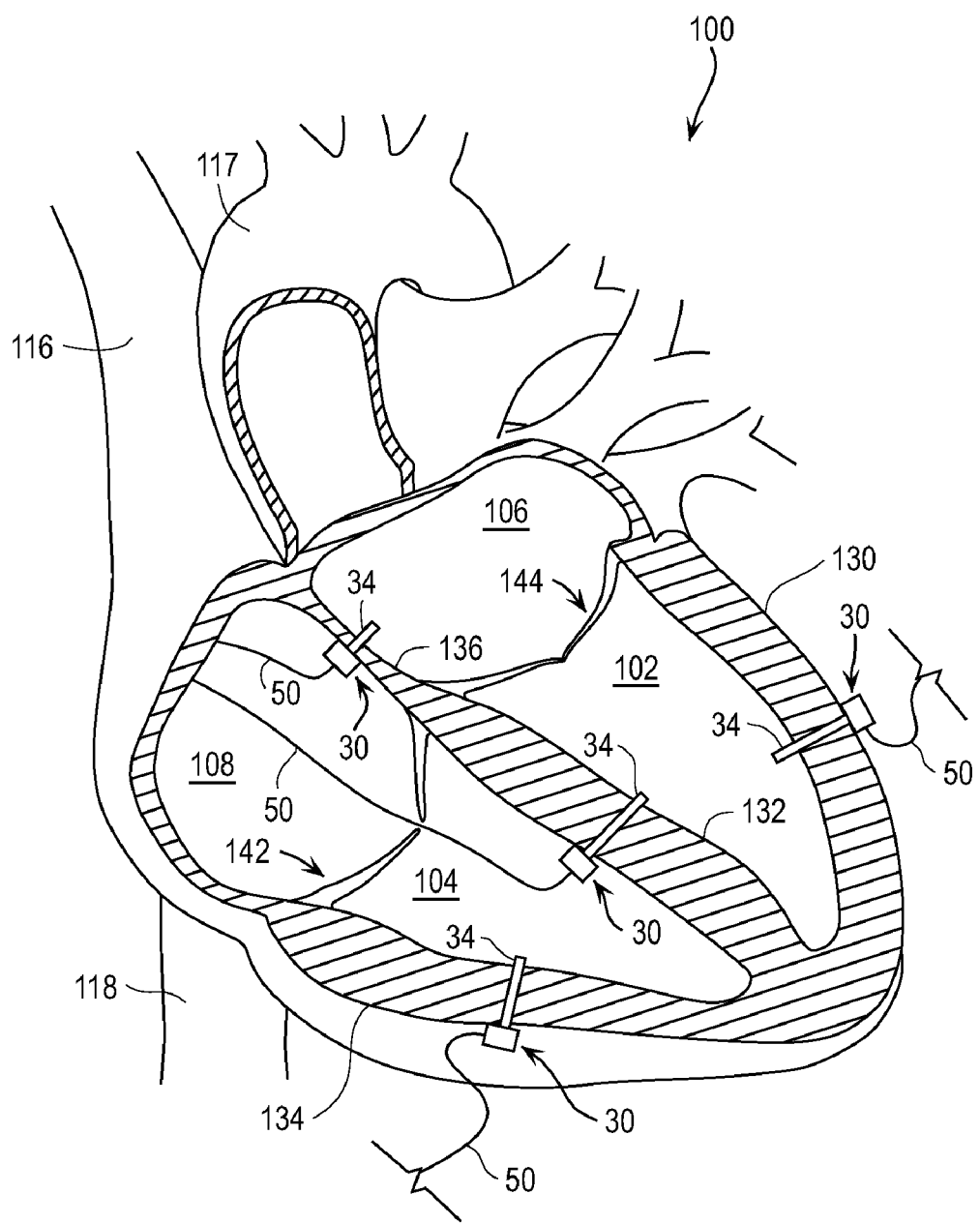
FIG. 2 is a schematic view illustrating various possible endocardial implant locations for the remote sensor assembly.

With reference to FIG. 2, various possible anatomical implant positions for the RSA 30 are shown. To facilitate a discussion of the various possible anatomical implant positions, the heart 100 is shown schematically. The heart 100 includes four chambers, including the left ventricle (LV) 102, the right ventricle (RV) 104, the left atrium (LA) 106, and the right atrium (RA) 108. The LV 102 is defined in part by LV wall 130, and the RV 104 is defined in part by RV wall 134. The LV 102 and the RV 104 are separated by ventricular septal wall 132, and the LA 106 and the RA 108 are separated by atrial septal wall 136.

The right atrium 108 receives oxygen deprived blood returning from the venous vasculature through the superior vena cava 116 and inferior vena cava 118. The right atrium 108 pumps blood into the right ventricle 104 through tricuspid valve 142. The right ventricle 104 pumps blood through the pulmonary valve and into the pulmonary artery which carries the blood to the lungs. After receiving oxygen in the lungs, the blood is returned to the left atrium 106 through the pulmonary veins. The left atrium 106 pumps oxygenated blood through the mitral valve 144 and into the left ventricle 102. The oxygenated blood in the left ventricle 102 is then pumped through the aortic valve, into the aorta 117, and throughout the body via the arterial vasculature.

By way of example, not limitation, the RSA 30 may be implanted such that the distal end of the PTC 34 resides in any chamber of the heart 100, such as the LV 102 or the LA 106, for example, although the LV 102 is preferred for some clinical applications. For example, the PTC 34 may be positioned across the LV wall 130 such that the distal end of the PTC 34 is disposed in the LV 102 as described with reference to FIG. 1. As an alternative, the PTC 34 may be positioned across the RV wall 134 such that the distal end of the PTC 34 is disposed in the RV 104. As a further alternative, the PTC 34 may be positioned across the atrial septal wall 136 or the ventricular septal wall 132 such that the distal end of the PTC 34 is disposed in the LA 106 or LV 102, respectively. If the ITD 20 comprises a unitary structure containing both the RSA 30 and the TU 40, the ITD 20 may be positioned in the same manner as the RSA 30 or it may be entirely disposed within a heart chamber.

Although endocardial implant sites are shown and described herein, the RSA 30 may be implanted such that the PTC 34 extends through a vascular wall and into a vascular lumen, with the RSA housing 32 and associated components disposed outside the vascular wall. Further aspects of this vascular approach are described in U.S. Provisional Patent Application No. 60/440,151, filed Jan. 15, 2003, entitled Therapeutic Device and Method Using Feedback from Implantable Sensor Device, the entire disclosure of which is incorporated herein by reference.

B. Communication Techniques

The telemetry unit or communication circuit 40 wirelessly transmits pressure information from ITD 20 to collection system 60 (or other receiver, transceiver, transponder, or communication device) by radio telemetry or any other wireless data communication technique. In one embodiment, telemetry unit 40 includes or is coupled to an antenna for wireless communication. However, the antenna need not be located within telemetry unit 40. In another embodiment, telemetry unit 40 also includes signal processing circuits, such as amplification and filtering circuits that process the electrical pressure signal received from pressure transducer or remote sensor assembly (RSA) 30, or analog-to-digital conversion circuits, or a microprocessor or other circuit for performing data analysis or data compression. In a further embodiment, telemetry unit 40 also includes a memory device for storing the pressure information, other data, or operating parameters of system 10. In yet another embodiment, telemetry unit 40 includes a real-time clock for time-stamping the pressure information.

In one embodiment, at least one of telemetry unit 40 or RSA 30 is powered by an internal power source such as a lithium or other suitable battery. In another embodiment, telemetry unit 40 is a passive transponder that is not powered by an internal power source. Instead, telemetry unit 40 receives energy wirelessly from a remote source, such as an energy source external to the body of the patient in which ITD 20 is implanted. Telemetry unit 40 is powered by the energy that it receives wirelessly from the external source. In another embodiment, the battery is rechargeable and ITD 20 includes an energy reception circuit that is coupled to the battery. The energy reception circuit in ITD 20 wirelessly receives energy from a remote source, such as an energy source that is external to the body of the patient in which ITD 20 is implanted. The energy that is received by the energy reception circuit in ITD 20 is used by the energy reception circuit to recharge the battery.

In one example of passive transponder technology, telemetry unit 40 includes a first inductance, such as a coil. A second inductance, such as a coil, is placed outside the body, for example, at a location that is close to the site of the implanted device. The first and second inductances are inductively coupled for wireless energy transmission from the external second inductance to the implanted first inductance, and for wireless data communication from the implanted first inductance to the external second inductance. System 10 may incorporate other passive transponder techniques as well.

In this document, wireless communication refers to any communication technique that does not use a wire or optical fiber. Wireless communication includes either or both of unidirectional and/or bidirectional communication. The unidirectional or bidirectional communication is carried out between any combination of implanted and/or external communication devices. In various embodiments, certain ones of the communication devices are carried by implanted medical devices (including, without limitation, implanted drug-delivery devices, implanted diagnostic devices such as an implanted pressure monitor, and implanted therapeutic devices such as a cardiac rhythm management device, a pacemaker, or a defibrillator), and external communication devices for communication therebetween. Wireless communication includes, but is not limited to, radio telemetry and reactive coupling. In one embodiment, wireless communication is used to program operating parameters in implanted ITD 20.

As illustrated in FIG. 1, the HDCS 60 is an external programmer device that includes a programmer transmitter or control transmitter 522 used to communicate with the receiver in the telemetry unit (TU) 40. The TU 40 operates on a battery. 47 CFR 95.628 allows the use of the 402–405 MHz frequency band and requires transmissions of bandwidth ≦300 KHz. The 3 MHz space from 402–405 MHz may be divided into n contiguous channels of (3÷n) MHz each, such as ten contiguous channels of 300 KHz each. The external programmer transmitter 522 of HDCS 60 sends a request signal on any one of the channels. The channels are scanned by the implant receiver of the TU 40 for the signal from the transmitter 522. After a suitable signal is detected by the implant receiver, the channel is used for the implant transmitter in the telemetry unit 40 of the medical system 10 to transmit data to the external receiver 524 of the programmer device 60.

Embodiments are directed to apparatus and methods of minimizing current drain of an implantable medical device during wireless communication with the device, thereby reducing battery depletion of the device. Some of the techniques are directed to reducing the complexity and average current drain of the implantable medical device. Other techniques are designed to reduce battery depletion for each scan of the channels.

1. Communication Channel Scanning Protocol

To reduce current drain of the implant receiver, the receiver may be configured to scan the communication channels at predetermined time intervals to listen for the programmer's request. This periodic scanning for signals may be performed to coincide with scheduled transmissions of the programmer device at a relatively slow rate such as once per hour. A scan may comprise a single sequence through the channels where each communication channel is received long enough to determine if there is a transmission from the programmer device. Alternatively, where time synchronization between the programmer and the implant is less accurate, a scan may comprise a string of sequences repeated at least once every five seconds, for example, pursuant to FCC MICS regulation, 47 CFR § 95.1209-d, since the programmer cannot transmit for longer than 5 seconds without sending data. Of course, different predetermined time intervals for scanning may be used. Scanning in accordance with the predetermined time intervals helps reduce the average current drain and complexity of the implant receiver.

In a time-based predictive approach, the implant receiver may perform a scan or series of scans at a predetermined time arranged in a previous communication with the programmer. For instance, the implant receiver may be equipped with a real time clock to scan at midnight, 2 a.m., 4 a.m., 6 a.m., and 8 a.m. for home monitoring. The synchronization of the communication between the programmer or control transmitter and the implant receiver can greatly reduce the on-time. A backup plan may be implemented to provide monitoring in the event that the intended communication at the primary predetermined time was not established. One example of a backup plan is for the implant receiver to scan at a secondary pre-arranged time. Another backup plan may be to employ periodic scanning at preset time periods as described above. Another backup plan may be to manually intervene and communicate with the implant via an alternate means, such as with a magnet, to resynchronize the implant and the programmer.

2. Communication Channel Selection

Another way to reduce battery depletion of the implant receiver is to reduce the number of channels that need to be scanned. The programmer may be designed to transmit the request on the channel used in the last communication session unless that channel was not suitable. For instance, the channel may have more interference than MICS regulations allowed or some other preset interference requirements that may be more stringent. In that case a lower-interference channel needs to be used. A common priority can be established for both the programmer and the implant receiver for the selection of alternative channels. For example, the second-to-last channel used may be the next choice.

Alternatively, with each communication session, the programmer transmission could include instructions for one or more alternate channels to be used if the primary (last used) channel had excessive interference. These channels and their priority order would be selected based on the programmer's measurement of channel interference prior to the communication session. The selections may be based on one interference measurement immediately prior to the communications session or on statistical combination of multiple measurements over time.

This priority channel selection method allows the implant receiver to scan only one or more channels according to an order of priority that will minimize the receiver on-time. The order of priority may be based on factors such as the ambient power level of the other channels as previously measured and transmitted to the implant receiver by the programmer. As soon as the implant receiver receives the proper request on a channel, it will power down and instruct the implant transmitter to send data on that channel, after a predetermined delay to allow for shut-down of the programmer transmitter. Any benefit of the priority channel selection method to reduce battery depletion is highly dependent on the specific scanning protocol used. To gain maximum benefit, the number of channels normally scanned may be greatly reduced. If there were little time-synchronization between the programmer and implant, then minimum battery depletion may be achieved by limiting the receiver scan to the last channel used unless a communication session has not been established within a predetermined maximum allowable length of time. In that case, one or more alternate channels will be scanned according to the preset order of priority. Alternatively, the programmer and implant may be time synchronized (e.g., at a predetermined time arranged in a previous communication). In this case, battery current would be minimized automatically since there would normally be a signal from the programmer on the first channel scanned such that the receiver can power down immediately.

In all cases, the programmer may aid in minimizing the implant receiver power drain by consistently using the same channel or channels. This can be achieved by transmitting on the "last channel" any time that channel is below the monitoring threshold power level rather than selecting the channel with the lowest interference which would result in much more channel switching.

3. Wideband Receiver

As an independent method of reducing battery depletion, the implant receiver may be configured as a wideband receiver. Instead of scanning a number of channels (e.g., 10 channels) using a scanning receiver, the wideband receiver will detect a request on any of the channels simultaneously and identify the channel to be used from the signal detected. The wideband receiver will be on for a shorter time than a scanning receiver and hence cause less battery depletion, since the additional on-time to scan multiple narrowband channels separately is eliminated. Moreover, the circuitry to implement the wideband receiver can be made simpler than that required to implement the scanning receiver.

Figure 3:
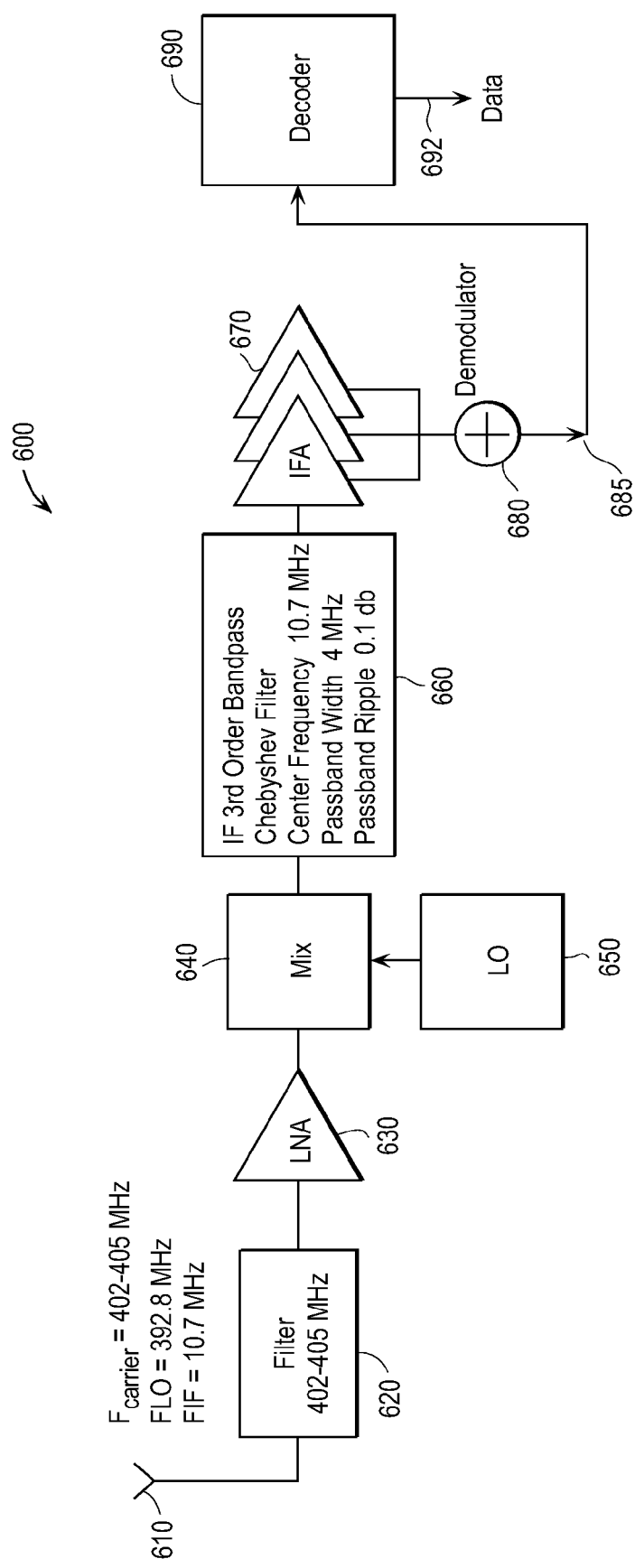
FIG. 3 is a block diagram of a wideband receiver for use as an implanted remote receiver according to another embodiment.

FIG. 3 is a block diagram of a portion of a wireless receiver that may be used in external or remote receiver 524 or other receivers consistent with embodiments of the present invention. Alternately, in a system supporting bidirectional communications, this receiver may be a portion of implant device 40. Included are a front-end filter 620, low noise amplifier (LNA) 630, mixer 640, local oscillator 650, bandpass filter 660, intermediate frequency amplifier 670, demodulator 680, and decoder 690.

Figure 4:
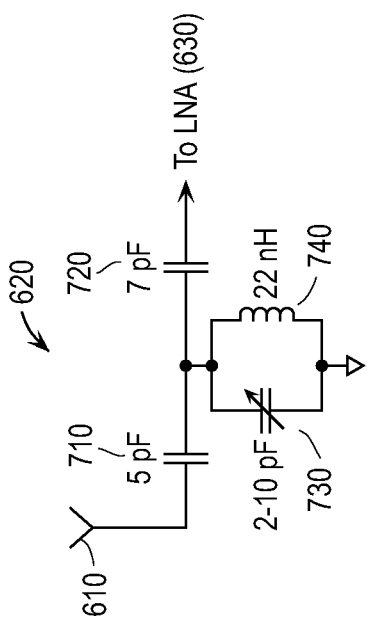
FIG. 4 is a circuit of a front-end filter in the wideband receiver of FIG. 3 according to an embodiment.

A signal is received on antenna 610 from a transmitter, such as the programmer transmitter 522. The received signal is filtered by front-end filter 620, which in turn drives low noise amplifier 630. The front-end filter 620 has a frequency range of 402–405 MHz. The front-end filter may be a surface-acoustic-wave filter, a discrete filter as shown in FIG. 4, or other similar types of filters. The low noise amplifier 630 amplifies the filtered signal and drives mixer 640.

Local oscillator 650 may include a synthesizer or phase-locked loop (PLL). The synthesizer or PLL adjusts the local oscillator (LO) signal to the correct frequency. An output of a voltage controlled oscillator (VCO) in the local oscillator 650 is divided in frequency and compared to a reference clock by a phase-frequency detector. This reference clock may be generated by an oscillator, such as a Colpits oscillator, crystal, or other stable clock source. The output of the phase-frequency detector is filtered to generate a control voltage, which adjusts the frequency of the VCO.

The output of local oscillator 650 is multiplied with the amplified received signal by the mixer 640. The mixer provides an output signal having components at frequencies equal to the sum of and difference of the frequencies of the received signal and the local oscillator signal. The local oscillator 650 may have a frequency of about 392.8 MHz in a specific embodiment. The lower of these frequencies is referred to as the intermediate frequency. The intermediate frequency is filtered by bandpass filter 660. In this way the received signal at the carrier frequency is demodulated to the intermediate frequency.

In a specific embodiment of the present invention, bandpass filter 660 is a third-order filter. In one embodiment, the center frequency is approximately 10.7 MHz, the passband width is about 4 MHz, and the passband ripple is about 0.1 dB. In other embodiments of the present invention, the filter may have different values for these parameters.

The output of the bandpass filter 660 drives the intermediate frequency amplifier 670. This amplifier may be a series of limiters or other amplifier stages. The output of each stage of the intermediate amplifier 670 drives a cell in the demodulator circuit 680. These cells may, for example, be gm cells (transconductance amplifiers) providing currents that are summed together and provided as a demodulator output on line 685.

The output of the intermediate frequency amplifier 670 drives demodulator 680. The demodulator demodulates the intermediate frequency signal at the output of the intermediate frequency amplifier 670 to baseband. The demodulator may be preferably configured to demodulate amplitude modulated signals but may be configured to demodulate frequency modulated signals in other embodiments. The decoder 690 receives the baseband signal and checks for a correct address and consistent data. If a signal having the correct address and consistent data is received, data is output on bus 692 indicating the receipt of valid data.

In one embodiment of the present invention, the LNA 630, mixer 640, local oscillator 650, intermediate frequency amplifier 670, and demodulator circuit 680 may be an integrated circuit such as the TH71101 available from Melexis Micro Electronics Integrated Systems, located at 41 Locke Road, Concord, N.H. 03301. In other embodiments, this or other portions of the circuit may be integrated on one or more integrated circuits.

FIG. 4 is a schematic of a circuit that may be used as the front-end filter 620 in FIG. 3, or as the front-end filter in other embodiments of the present invention. Included are coupling capacitors 710 and 720, and a tank circuit including capacitor 730 and inductor 740. In one embodiment of the present invention, tank capacitor 730 is a variable capacitor. Again, signals are received on antenna 610 from a wireless transmitter, such as a transmitter in implant system 10. In one embodiment of the present invention, antenna 610 is a printed circuit board strip line measuring between 0.8 and 1.0 inches.

Signals received on antenna 610 are passed by coupling capacitor 710 to the tank circuit. At resonant frequency, the impedance of the tank circuit is high, and frequencies near resonance are passed through coupling capacitor 720 to LNA 630. Signal frequency components that are away from the resonant frequency of the tank circuit see a low impedance, and thus pass through the tank to ground. That is, they are filtered and not passed to the LNA 630.

A specific embodiment of the present invention uses a tunable capacitor having values between 2 and 10 pF as tank capacitor 730, and an inductor having a value of 22 nH for tank inductor 740. If the variable capacitor is set at 7 pF, the tank circuit is resonant at approximately 400 MHz. It will be appreciated by one skilled in the art that other filters or structures, or similar filters having different values, may be used as front-end filter 620.

Figure 5:
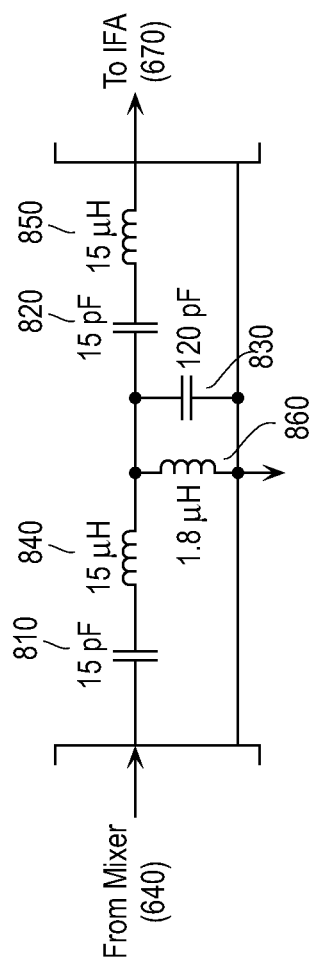
FIG. 5 is a circuit of a bandpass intermediate frequency filter in the wideband receiver of FIG. 3 according to an embodiment.

FIG. 5 is a schematic of a third-order bandpass filter that may be used as the third order bandpass filter 660 in FIG. 3, or as filters in other embodiments of the present invention. Included are series capacitors 810 and 820, and shunt capacitor 830, series inductors 840 and 815, and shunt inductor 860. A signal is received from the mixer 640 by series capacitor 810. The output of the filter drives the intermediate frequency amplifier 670, as shown in FIG. 3. It will be appreciated by one skilled in the art that other filters may be used. For example, an active filter may be used.

Figure 6:
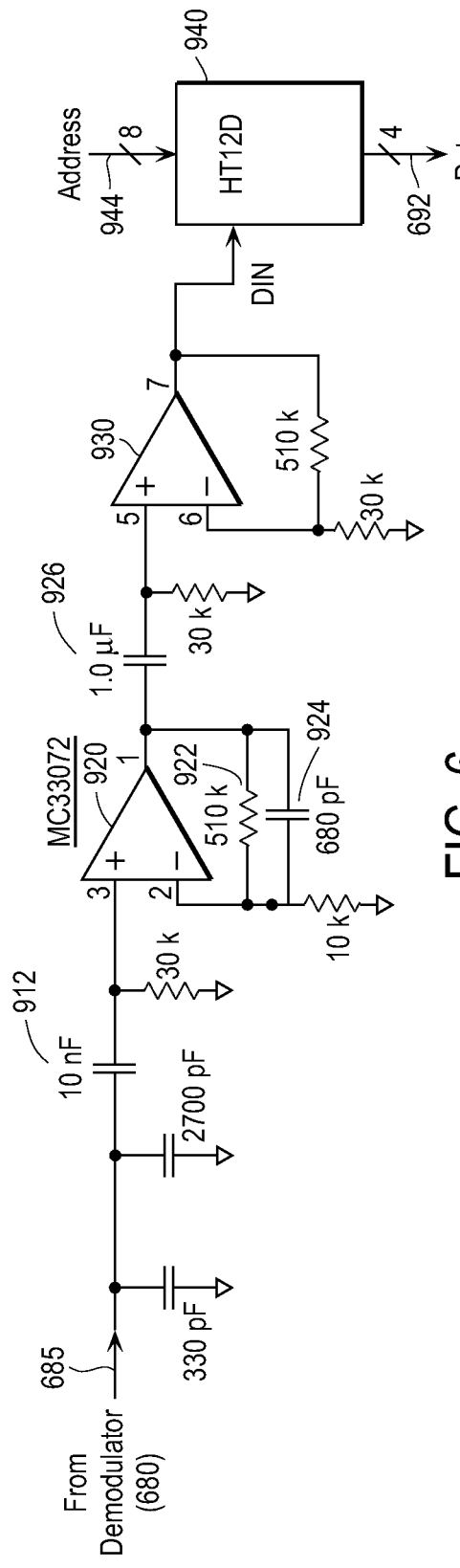
FIG. 6 is a circuit of a decoder in the wideband receiver of FIG. 3 according to an embodiment.

FIG. 6 is a schematic that may be used as the decoder 690 in FIG. 3, or as other decoders in other embodiments of the present invention. Signals are received from the demodulator 680 on line 685 and AC coupled to the amplifier 920 by coupling capacitor 912. Amplifier 920, along with filter components including resistor 922 and capacitor 924, filter intermediate frequency signal to baseband, essentially acting as an integrator. The output of the demodulator is AC coupled through coupling capacitor 926 to amplifier 930. The output of the amplifier drives decoder 940. In a specific embodiment, amplifiers 920 and 930 are integrated as a single integrated circuit, such as the MC33072, available from ON Semiconductor, located at 5005 East McDowell, Phoenix, Ariz. 85082.

In a specific embodiment of the present invention, decoder 940 is an HT12D decoder available from Holtek Semiconductor Inc. located at 3-272 Grande Vista Ave., Laguna Niguel, Calif. 92677. An address is presented to the decoder on bus 944. If the received signal from the comparator contains the correct address, and the same data is received three times in a row, the data is considered valid and output on bus 692. It is understood that FIG. 6 shows a specific embodiment, and does not limit the present invention.

There is a possibility that interference on any of the ten channels will mask a request from the programmer. The interfering signals are typically constant amplitude, frequency modulated signals. For amplitude-modulated transmission signals, experiments have confirmed that such transmission signals are tolerant of the constant-amplitude frequency-modulated interfering signals. Thus, the wideband receiver desirably is configured to receive an amplitude shift keyed (ASK) signal from the programmer.

The wideband receiver may have degraded SNR (noise performance) as compared to a narrowband receiver. The noise degradation of the wideband receiver of the implant may shorten the effective programmer-to-implant transmission range in air. Experiments have shown, however, that the range degradation is tolerable. For example, in one bench test with the transmitter immersed in a liquid representing the relevant properties of tissue, the range degraded from 3 meters for a receiver with 400 KHz bandwidth to 2.5 meters for a receiver with 4 MHz bandwidth.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A method for communication between an implantable medical device having a wireless receiver and a wireless transmitter and an external device having an external transmitter and an external receiver, the implantable medical device and the external device being configured to communicate wirelessly with one another via a plurality of communication channels each having a different frequency within a frequency band, the method comprising:

attempting initiation of a present communication session between the implantable medical device and the external device using a preset communication channel selected from the plurality of communication channels; and switching to an alternate communication channel for the present communication session according to an order of priority if the wireless receiver of the implantable medical device does not detect a suitable signal from the external transmitter of the external device using the preset communication channel;

wherein attempting initiation of the present communication session comprises selecting as the preset communication channel a last communication channel used in a last communication session immediately preceding the present communication session; and wherein switching to the alternate communication channel comprises selecting as the alternate communication channel a second-to-last communication channel used in a second-to-last communication session immediately preceding the last communication session.

2. The method of claim 1 wherein the order of priority of communication channels selected is based on communication channels used in previous communication sessions in reverse chronological order.

3. The method of claim 1 wherein the present communication session is initiated at a primary predetermined time arranged in a previous communication with the external device.

4. The method of claim 3 wherein the present communication session is initiated at a secondary predetermined time arranged in the previous communication with the external device if the wireless receiver fails to detect wirelessly a suitable signal from the external transmitter at the primary predetermined time.

5. The method of claim 3 initiating the present communication session comprises scanning with the wireless receiver for signals from the external transmitter at preset time periods if the wireless receiver fails to detect wirelessly a suitable signal from the external transmitter at the primary predetermined time.

6. The method of claim 1 wherein switching to the alternate communication channel comprises selecting a communication channel having a lowest channel interference as the alternate communication channel based on measurement of channel interference conducted prior to attempting initiation of the present communication session.

7. The method of claim 6 wherein the alternate communication is selected based on measurement of channel interference immediately prior to the present communication session.

8. The method of claim 6 wherein the alternate communication is selected based on a statistical combination of multiple measurements of channel interference over time prior to the present communication session.

9. The method of claim 1 wherein attempting initiation of the present communication session comprises selecting as the preset communication channel a last communication channel used in a last communication session immediately preceding the present communication session as long as the last communication channel provides a suitable signal which is below a monitoring threshold power level regardless of whether the last communication channel has a lower interference than the other communication channels.

10. A method for communication between an implantable medical device having a wireless receiver and a wireless transmitter and an external device having an external transmitter and an external receiver, the implantable medical device and the external device being configured to communicate wirelessly with one another via a plurality of communication channels each having a different frequency within a frequency band, the method comprising:

attempting initiation of a present communication session between the implantable medical device and the external device using a preset communication channel selected from the plurality of communication channels; and switching to an alternate communication channel for the present communication session according to an order of priority if the wireless receiver of the implantable medical device does not detect a suitable signal from the external transmitter of the external device using the preset communication channel;

wherein the order of priority of communication channels selected is based on communication channels used in previous communication sessions in reverse chronological order.

11. The method of claim 10 wherein attempting initiation of the present communication session comprises selecting as the preset communication channel a last communication channel used in a last communication session immediately preceding the present communication session.

12. The method of claim 10 wherein the present communication session is initiated at a primary predetermined time arranged in a previous communication with the external device.

13. The method of claim 12 wherein the present communication session is initiated at a secondary predetermined time arranged in the previous communication with the external device if the wireless receiver fails to detect wirelessly a suitable signal from the external transmitter at the primary predetermined time.

14. The method of claim 12 wherein initiating the present communication session comprises scanning with the wireless receiver for signals from the external transmitter at preset time periods if the wireless receiver fails to detect wirelessly a suitable signal from the external transmitter at the primary predetermined time.

15. The method of claim 10 wherein switching to the alternate communication channel comprises selecting a communication channel having a lowest channel interference as the alternate communication channel based on measurement of channel interference conducted prior to attempting initiation of the present communication session.

16. The method of claim 15 wherein the alternate communication is selected based on measurement of channel interference immediately prior to the present communication session.

17. The method of claim 15 wherein the alternate communication is selected based on a statistical combination of multiple measurements of channel interference over time prior to the present communication session.

18. The method of claim 10 wherein attempting initiation of the present communication session comprises selecting as the preset communication channel a last communication channel used in a last communication session immediately preceding the present communication session as long as the last communication channel provides a suitable signal which is below a monitoring threshold power level regardless of whether the last communication channel has a lower interference than the other communication channels.

* * * * *